United States Patent [19]

Perry

[11] Patent Number: 4,678,331
[45] Date of Patent: Jul. 7, 1987

[54] MULTICUVETTE ROTOR ASSEMBLY
[75] Inventor: Matthew J. Perry, Libertyville, Ill.
[73] Assignee: Baxter Travenol Laboratories, Inc., Deerfield, Ill.
[21] Appl. No.: 623,057
[22] Filed: Jun. 21, 1984
[51] Int. Cl.$^4$ ............................................. G01N 21/07
[52] U.S. Cl. .................................... 356/246; 356/427; 356/440
[58] Field of Search ....................... 356/246, 427, 440; 250/576

[56] References Cited
U.S. PATENT DOCUMENTS
4,373,812 2/1983 Stein et al. ........................... 356/246

*Primary Examiner*—Davis L. Willis
*Assistant Examiner*—Matthew W. Koren
*Attorney, Agent, or Firm*—Susan B. Fentress; Paul C. Flattery

[57] ABSTRACT

An improved analytical cuvette rotor assembly for use in a centrifugal chemistry analyzer comprising a disc-shaped body having a plurality of radially extending compartments for retaining fluids. Sample fluids and reagent fluids contained in the compartments prior to centrifugation are separated by a novel dam structure extending between upper and lower surfaces of each compartment such that the premature mixing of sample and reagent fluid is significantly retarded. The dam, in cooperation with the compartment walls, further defines a fluid transfer passage that permits fluid to be transferred over the dam under analyzer operating rotational speeds.

3 Claims, 8 Drawing Figures

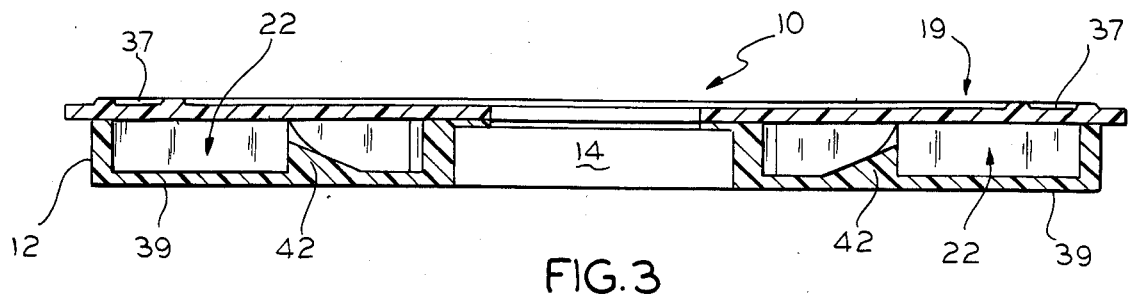
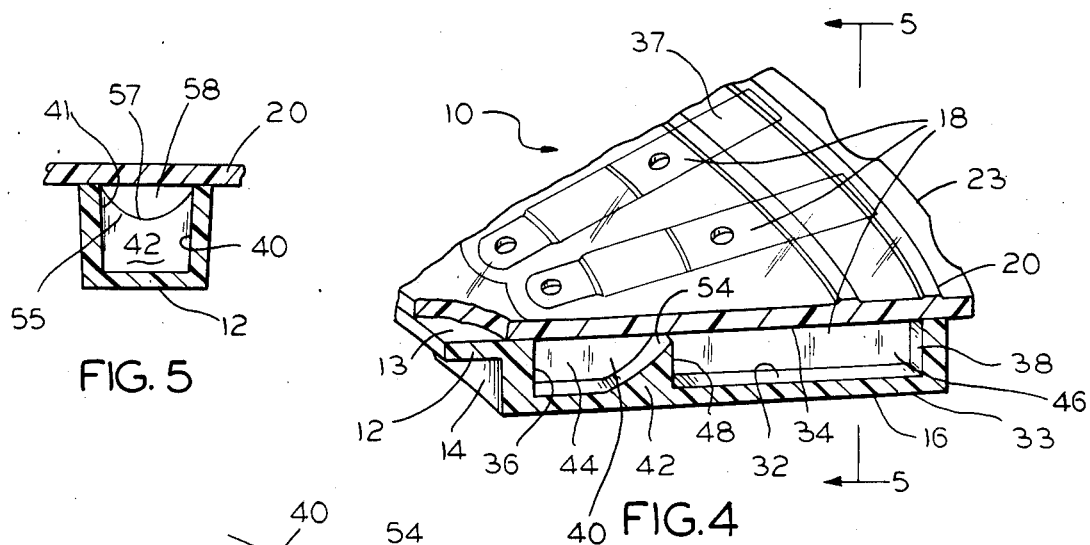

MULTICUVETTE ROTOR ASSEMBLY

BACKGROUND OF THE INVENTION

This invention relates to an improved cuvette rotor assembly used in centrifugal chemistry analyzers for the determination of a variety of serum constituents in the clinical laboratory. In particular, the invention relates to a cuvette rotor assembly having a significantly improved dam which prevents premature mixing of chemical reagents with a patient's serum or other biological fluid.

Conventional cuvette rotor assemblies such as those described in U.S. Pat. Nos. 4,123,173, 4,226,531, 4,314,970, and 4,373,812 generally comprise a disc-shaped body having about 20 space-apart recesses extending radially throughout its periphery in a circumferentially structured array. Each of the radially extending recesses (cuvettes) has fluid-filling ports or a slot in the top wall into which a patient's sample and chemical reagent are dispensed. A generally wedge-shaped barrier structure (dam) is disposed in said recess intermediate the fluid-filling passages such that the two fluids dispensed on each side of the barrier structure are kept separate from one another when the cuvette rotor is at rest.

After loading of the cuvettes is completed, the assembly is placed in a centrifugal analyzer and spun at a rotational speed of about 4,000 revolutions per minute for a period of time sufficient to effect transfer of fluid over the barrier structure and cause mixing of patient's sample with the chemical reagent. The rotational speed is then generally reduced to about 1,000 revolutions per minute and photometric measurements are made to determine the level of chemical constituent in the patient's sample. The operation of the centrifugal analyzer, the loading of the fluids in the cuvettes, and the overall construction of cuvette rotor assemblies similar to that described herein are generally well-known and do not constitute part of the present invention.

Premature mixing of a patient's sample with chemical reagents has been observed with various degrees in the cuvette rotors described hereinabove and those presently used in the clinical laboratory. Various modifications have been made to these cuvette rotors to reduce this premature mixing; however, none of these attempts have been effective in preventing this mixing. One such attempt is described in U.S. Pat. No. 4,373,812 and comprises a cuvette assembly having capillary flow inhibiting structures along the intersections between the compartment sidewalls and bottom surface, and along the substantially vertical wall portion of the dam. These capillary flow inhibiting structures, smoothly curved surface portions having a radius of curvature greater than 0.75 millimeters, are intended to retard spontaneous "creep" flow of fluid in either direction over the dam as the fluids are dispensed into the cuvette rotor at rest. Although this cuvette design somewhat retards premature mixing, it does not effectively eliminate the premature mixing and the possible cause of undesirable deviations in clinical assay values encountered with this type of cuvette rotor.

In accordance with the present invention, an improved cuvette rotor is described having a barrier structure (dam) capable of significantly retarding the premature mixing of chemical reagents and patients' samples in a centrifugal chemistry analyzer. The cuvette assembly of the present invention advantageously reduces the possibility of undesirable deviations in clinical assay values which may result from this premature mixing.

SUMMARY OF THE INVENTION

In accordance with the present invention, disclosed is a cuvette rotor for use in a centrifugal chemistry analyzer, said rotor having a substantially circular body member with a plurality of recesses circumferentially spaced about a central portion thereof, and a cover member disposed on at least a peripheral portion of each recess; the improvement comprising a barrier member disposed within each recess defining an inner chamber radially disposed toward the center of said rotor and an outer chamber radially disposed toward the peripheral portion of said rotor such that the inner surface of said barrier member forms the outer boundary of said inner chamber, and the outer surface of said barrier member forms the inner boundary of said outer chamber; wherein the upper edge of said barrier outer surface is lower at the interior portion than at the lateral edge portions thereof.

In accordance with an alternate embodiment of the present invention, disclosed is a multicuvette rotor for use in a centrifugal chemistry analyzer comprising a substantially circular body member having a substantially planar upper surface, a lower surface, and a plurality of spaced apart recesses extending radially in the peripheral portion thereof; a substantially circular cover member disposed adjacent the planar upper surface of said body member such that a plurality of enclosed chambers are defined by said cover member and said recesses; said cover member having an upper surface, a substantially planar lower surface, and a plurality of apertures through said cover member for filling the chambers with fluid; each of said enclosed chambers having a top wall defined by said cover member, a bottom surface defined by the bottom wall of said body member, an inner end wall disposed toward the center of said body member, an outer end wall disposed at the periphery of said body member, sidewalls extending radially between said inner and outer end walls, and a barrier member disposed between said end walls and sidewalls; said barrier member having an upstanding wall portion defining an inner chamber disposed toward the central portion of said body member, and an outer chamber disposed toward the peripheral portion of said body member, said wall portion having lateral edges disposed adjacent the radially extending chamber sidewalls and extending from the bottom surface of said chamber to an area substantially adjacent the lower surface of said cover member; said apertures positioned in said cover member so that said inner and outer chambers may be independently filled with fluid; said barrier member further comprising an inclined ramp surface having a lower edge portion disposed adjacent the bottom surface of said inner chamber, lateral edge portions disposed adjacent the radially extending chamber sidewalls, an upper edge portion defining the intersection between the vertical wall portion and inclined ramp surface, and a fluid transfer passage defined by the top of said vertical wall portion and the lower surface of said cover member; wherein the upper edge portion of said upstanding wall is lower at the interior portion than at the lateral edges adjacent said chamber sidewalls.

BRIEF DESCRIPTION OF THE DRAWINGS

FIG. 3 is sectional view of the assembly taken along line 3—3 of FIG. 1;

FIG. 4 is a perspective view of a portion of the rotor assembly shown in FIG. 1;

FIG. 5 is a sectional view of the assembly taken along line 5—5 of FIG. 4;

FIG. 6 represents an enlarged perspective view of the barrier member shown in FIG. 4;

FIG. 7 represents an enlarged perspective view of an alternate barrier member shown similarly in FIG. 6;

FIG. 8 represents an enlarged perspective view of an alternate barrier member shown similarly in FIGS. 6 and 7.

DETAILED DESCRIPTION OF THE PREFERRED EMBODIMENT

In accordance with the present invention, improved cuvette rotor assemblies are disclosed for use in centrifugal chemistry analyzers. These rotors may be flexible, rigid, disposable, resuable, plastic, or metal. In general, the cuvette rotor assembly includes a disc-shaped body having a plurality of spaced-apart recesses circumferentially spaced about a central hub and a cover which closes off at least a portion of each recess. Each recess contains a dam-like barrier disposed therein to separate fluids prior to centrifugation. In particular, the present invention provides an improved barrier for cuvette rotors such as those disclosed in U.S. Pat. Nos. 4,123,173, 4,226,531, 4,314,970, and 4,373,812. Although the following detailed description of a preferred embodiment of the present invention describes a specific type of cuvette rotor, it is to be understood that this embodiment was chosen to illustrate the structure and function of the barrier and not to limit the invention to any particular rotor design generally found useful in centrifugal chemistry analyzers.

Figure 1:
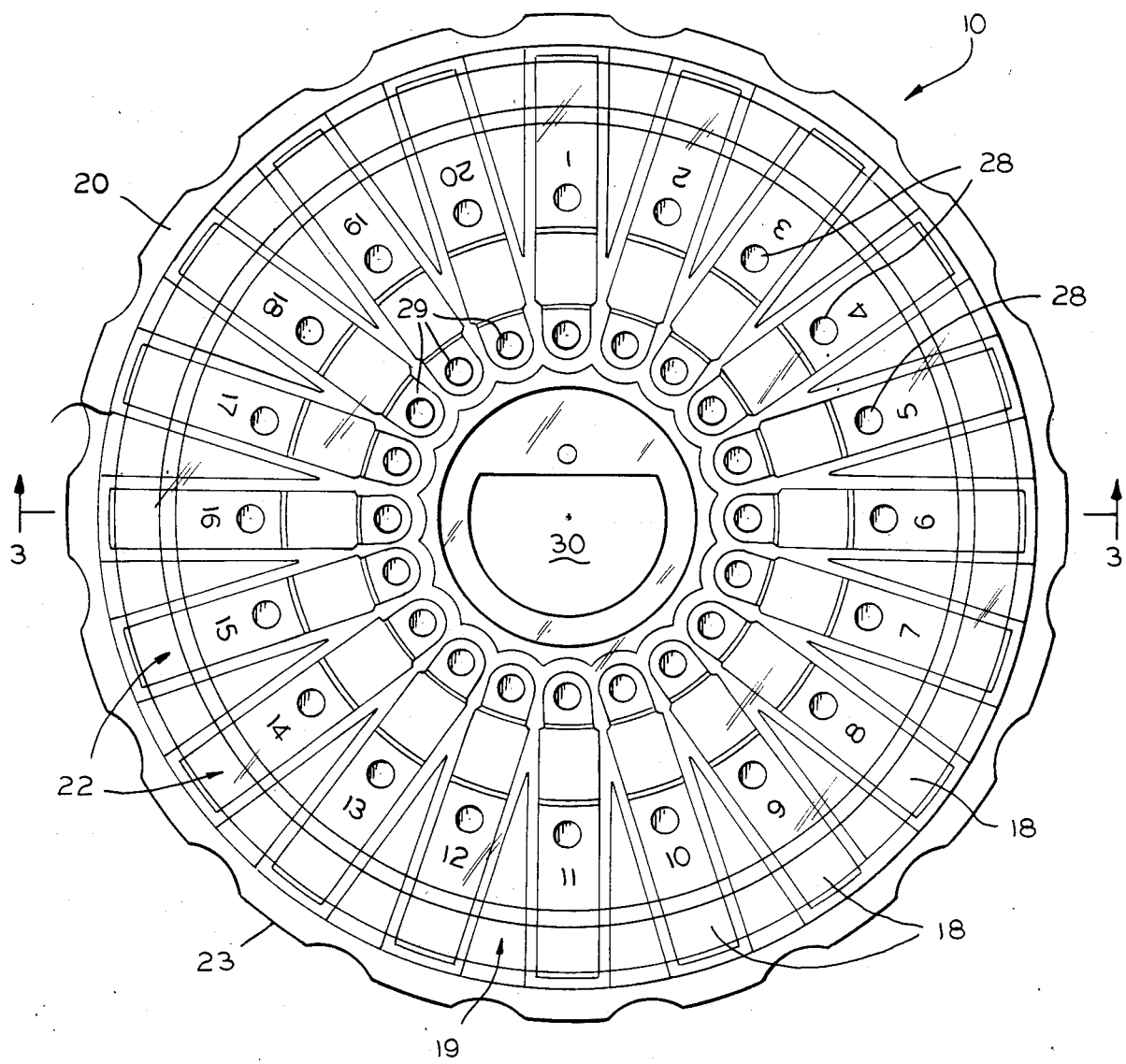
FIG. 1 is a top plan view of a multicuvette rotor assembly in accordance with one embodiment of the present invention.
Figure 2:
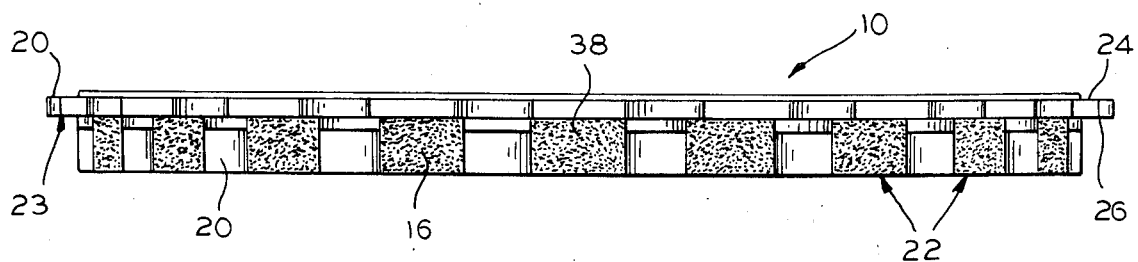
FIG. 2 is a side elevational view of the assembly shown in FIG. 1.

Referring to FIGS. 1 through 4, a multicuvette rotor assembly in accordance with one embodiment of the present invention is generally shown at 10. This type of rotor, which is preferably injection molded, can be made from a variety of transparent plastic resins, and is intended to be disposable to reduce cross-contamination of patients' samples. The rotor may be made from ultraviolet transmitting materials such as acrylics, polyolefins, styrenes, polyesters, polycarbonates, and the like.

The rotor assembly is generally constructed of a substantially flat, circular or disc-shaped body member 12 which defines the lower base portion of the assembly 10. The body member has a substantially planar upper surface 13 adapted to receive a substantially flat circular cover member 20, described hereinafter. The upper surface is preferrably flat within normal molding tolerances. The body member further comprises a hub portion 14 disposed in its center for positioning the assembly 10 in the centrifugal analyzer (not shown).

The body member further includes a lower surface 16 and a plurality of spaced apart recesses 18 extending radially from the central hub portion 14 to the peripheral portion generally shown at 19, and vertically between its lower surface 16 to its planar upper surface 13. These recesses are elongated and are generally rectangular or wedge-shaped. Preferably they extend from the hub portion 14 to the periphery of the body member. The optical path inside the rotor (the distance between surfaces 32 and 34, described hereinafter) is preferably about 0.197 inches.

A substantially circular cover member 20 is secured to the planar upper surface 13 of the body member such that the cover member provides a top for and encloses the recesses 18 to form enclosed chambers 22. In the preferred embodiment of the present invention, this cover member is permanently joined to the upper surface 13 of the body member with adhesive or by ultrasonic welding. The diameter of the cover member is slightly larger than the diameter of the body member to provide a flange 23 at its periphery for grasping and handling the rotor. In the most preferred embodiment of the present invention, this flange 23 is scalloped.

The cover member has an upper surface 24, a substantially planar lower surface 26, and a plurality of apertures (ports) 28 and 29 extending through the cover member. These apertures are paired such that each enclosed chamber 22 has at least two apertures disposed in its top wall. The apertures 28 disposed in the peripheral portion 19 of the cover member may be used for filling the chambers 22 with liquid chemical reagents, and the apertures 29 disposed toward the central hub portion 14 may be used for filling the chambers 22 with a patient's samples of a biological fluid. As will be appreciated hereinafter, the apertures 28 and 29 are positioned in said cover member 20 so that the patient's sample fluid and the liquid chemical reagent may be independently loaded into the cuvette assembly 10. The cover member is further formed with a D-shaped central opening 30 to facilitate its secure location in the centrifugal analyzer.

Referring to FIG. 4, each of the enclosed chambers 22 comprises a bottom surface 32, defined by the bottom wall 33 of the body member, a top wall 34 bounded by the lower surface 26 of the cover member 20, an inner end wall 36 disposed toward the center hub portion 14 of the body member, an outer end wall 38 disposed toward the outer periphery of said body member, and sidewalls 40 and 41 extending radially between said inner 36 and outer 38 end walls. The respective chambers 22 are constructed such that the recesses 18 are preferably substantially enclosed, with the exception of the fluid filling apertures 28 and 29. It will be appreciated, however, that chambers constructed in alternate rotor types, such as those described in U.S. Pat. No. 4,123,173, will have a cover portion which only partially encloses the chamber at the peripheral portion.

In accordance with the present invention, photometric measurements can be made in the absorbance mode where the light is transmitted through the top and bottom walls of the chamber such as at 37 and 39, or alternatively in the fluorescent or light scattering mode where the light is directed through the outer end wall 38. In the fluorescent or light scattering mode, the outer endwall 38 is optically transparent and has an optical surface finish. As is generally well understood in the art, this can be accomplished from a diamond polish in the mold.

A barrier member 42 is positioned intermediate the end walls 36 and 38 and extends laterally between the sidewalls 40 and 41 to form a dam-like structure. The positioning of this barrier member 42 between the endwalls creates an inner chamber 44 disposed toward the central portion of the body member, and an outer chamber 46 disposed toward the peripheral portion of the body member. This barrier member 42 divides the cuvette chambers 22 into inner 44 and outer 46 chambers to separate the patient's sample from the chemical reagent dispensed therein while the cuvette rotor assembly is at rest. The outermost edge of the barrier member is preferably about 0.7 inches from the outer end wall 38 and about 0.6 inches from the inner end wall 36. These distances may vary and are generally dependent upon the volume requirements for sample and reagent. Under analyzer operating rotational speeds, the outer chamber becomes the photometric measuring chamber. The apertures 28 and 29 are positioned over the outer and inner chambers respectively such that the chambers may be independently filled with fluid.

Referring now to FIG. 6, the barrier member 42 is generally wedge-shaped and includes upstanding wall portion 48 extending from the bottom surface 32 of the chamber 22 to a height sufficient to separate the fluids into the inner and outer chambers. The minimum height of this wall portion at its centermost interior portion 57 is generally chosen such that premature mixing of fluids is prevented or retarded, and the maximum height is chosen to insure adequate mixing of fluids during centrifugation. Thus, preferably the range of wall heights at the interior 57 is from about 0.095 inches to about 0.120 inches. Preferably, the wall height is about 0.110 inches.

The upstanding wall generally has from about a 2° to about a 5° draft from vertical, and is more preferably about 5° from vertical. In a more preferred embodiment of the present invention, this upstanding wall is substantially vertical. The lateral edge portions 52 and 53 of the upstanding wall 48 are disposed adjacent the radially extending sidewalls 40 and 41, and extend from the bottom surface 32 of the chamber to an area substantially adjacent the surface 34 bounded by said cover member. The lateral edge portions preferrably extend from about 90 to about 100% of the depth of the chamber between surfaces 32 and 34. In a more preferred embodiment of the present invention, the lateral edges 52 and 53 of the upstanding wall extend the entire distance (about 100%) between the bottom surface 32 of the chamber to the surface 34 bounded by the cover member 20.

The barrier member further includes a ramp surface 54 which is inclined with respect to the bottom surface 32 and extends upwardly between the bottom surface of the inner chamber 44 to the top edge 55 of the upstanding wall 48. The slope of the ramp is dependent upon the height of the upstanding wall at its center. Preferably, the overall slope is from about 21° to about 26°, and more preferably about 24°. The lower edge portion 56 of the ramp surface may extend to the top edge of the upstanding wall in a continuously sloping manner, or it may extend discontinuously. In a more preferred embodiment of the present invention, the inclined ramp surface 54 slopes continuously from the lower edge portion 56 adjacent to the bottom surface to the top edge 55 of the upstanding wall.

The barrier member 42 of the present invention includes a fluid transfer passage 58 defined by the top edge 55 of the upstanding wall portion 48 and the lower surface 34 bounded by the cover member 20. In a preferred embodiment of the present invention, the distance between the top edge 55 at its center 57 and the lower surface 34 of the cover member is from about 0.073 inches to about 0.106 inches. More preferably, this distance is about 0.087 inches. In the embodiment, shown in FIGS. 5 and 6, the interior portion 57 of the upstanding wall 48 has a height which is lower than the lateral edge portions 52 and 53 which are shown extending the entire upstanding distance of the recess. As a result, the top edge 55 is curvilinear and forms an arcuate crest over which the fluid is transferred from the inner chamber 44 to the outer chamber 46 at fluid transfer effecting analyzer rotational speeds. This curvilinear edge 55 thus facilitates mixing of the fluids.

It will be appreciated that in accordance with a more preferred embodiment of the present invention, the fluid transfer passage 58 is bounded solely by the top edge 55 of the upstanding wall 48 and the lower surface 34 of the cover member. This embodiment is illustrated in FIGS. 6, 7, and 8.

In accordance with the present invention, we have advantageously found that by increasing the height of the top edge 55 of the barrier member at the lateral edge portions 52 and 53 to the top of the chamber 22 relative to the center of the wall 48, fluid cannot pass over or creep over the top of the barrier when the rotor is at rest. Moreover, we have found that by providing a contoured or scooped shape to the ramp surface, that fluid flow over the barriers is facilitated during rotor operation.

In an alternate embodiment of the present invention, the top edge of the upstanding wall 48 intersecting the ramp surface 54 depends downwardly from the elevated lateral edges 52 and 53 to the lower interior portion in a linear fashion. In FIG. 7, an upstanding wall portion of the barrier member is shown having a generally V-shaped top edge 60 forming the bottom of the fluid transfer passage 58. It should be pointed out however, that in the embodiments shown in FIGS. 5, 6 and 7, the lowermost portion of the top edge 60 may be substantially flat at the interior portion. That is, both the slope and length of the downwardly depending top edge portions 61 and 63 may vary while retaining their effectiveness in preventing premature mixing of fluids in accordance with the present invention.

The ramp surface of the embodiment shown in FIG. 7 is contoured as a result of the increased height of the upstanding wall at its lateral edges. The ramp surface 54 preferrably extends inwardly from each of the lateral edge portions, shown at 62 and 63, and depends downwardly to the interior portion of the ramp surface.

In another alternate embodiment of the present invention, the barrier member 42 comprises a substantially flat interior ramp surface 70 much like the ramp surface found in conventional cuvette rotors flanked on either side by a pair of wedge-shaped columns 72 and 73 disposed adjacent sidewalls 40 and 41 and extending upwardly toward the top of the chamber. In the most preferred embodiment, the wedge-shaped columns have an inclined upper ramp surface 74 which extends inwardly in a horizontal manner from each of the lateral edge portion to a first 76 and second 78 vertically depending inner sidewall. The distance between the chamber sidewalls (40 and 41) and the vertically depending inner sidewalls (76 and 78) may vary while retaining the ability to effectively prevent premature mixing of fluids in accordance with the present invention. These inner sidewalls extend from the upper ramp surface of the columns downwardly to the interior ramp surface 70. The upstanding wall portion 48 of this barrier member is generally U-shaped, and the fluid passageway is substantially rectangular. The lateral portions 79 and 80 of the wall portion 48 are preferably flat.

Although the present invention has been described in detail with specific reference to its preferred embodiment, it will become obvious to one having ordinary skill in the art to make various modifications and changes thereto without departing from the spirit and scope of the invention.

I claim:

1. A multicuvette rotor for use in a centrifugal chemistry analyzer comprising:

a substantially circular body member having a substantially planar upper surface, a lower surface, and a plurality of spaced apart recesses extending radially in the peripheral portion thereof;

a substantially circular cover member disposed adjacent the planar upper surface of said body member such that a plurality of enclosed chambers are defined by said cover member and said recesses;

said cover member having an upper surface, a substantially planar lower surface, and a plurality of apertures through said cover member for filling the chambers with fluid; each of said enclosed chambers having a top wall defined by said cover member, a bottom surface defined by said body member, an inner end wall disposed toward the center of said body member, an outer end wall disposed at the periphery of said body member, sidewalls extending radially between said inner and outer end walls, and a barrier member disposed between said end walls and sidewalls;

said barrier member having an upstanding wall portion defining an inner chamber disposed toward the central portion of said body member, and an outer chamber disposed toward the peripheral portion of said body member;

said apertures positioned in said cover member so that said inner and outer chambers may be independently filled with fluid;

said barrier member further comprising an inclined ramp surface having a lower edge portion disposed adjacent the bottom surface of said inner chamber, lateral edge portions disposed adjacent the radially extending chamber sidewalls, an upper edge portion defining the intersection between the upstanding wall portion and inclined ramp surface, and a fluid transfer passage defined by the top of said upstanding wall portion and the lower surface of said cover member, and wherein the ramp surface extends inwardly from each of the lateral edge portions to a first and second vertically depending inner sidewall respectively, said inner sidewall extending from the lateral edge ramp surface downwardly to an interior ramp surface extending between said inner sidewalls; and wherein the lateral edges of said upstanding wall portion disposed adjacent the radially extending chamber sidewalls extend from the bottom surface of said chamber to an area substantially adjacent the lower surface of said cover member.

2. The cuvette rotor of claim 1 wherein the ramp surface at the lateral edge portions is substantially horizontally disposed between the chamber sidewalls and the vertically depending inner sidewalls; and the upstanding wall portion of said barrier member is U-shaped.

3. The cuvette rotor of claim 1, wherein the ramp surface extends inwardly from each of the lateral edge portions and depends downwardly to the interior portion of said ramp and wherein the upstanding wall portion of said barrier is V-shaped.

* * * * *